US009267916B2

(12) United States Patent
Sévigny (10) Patent No.: US 9,267,916 B2
(45) Date of Patent: Feb. 23, 2016

(54) ELECTROPHORESIS BUFFER FOR FASTER MIGRATION, IMPROVED RESOLUTION AND EXTENDED SHELF-LIFE

(71) Applicant: DGel Electrosystem Inc., Montréal (CA)

(72) Inventor: Pierre Sévigny, Montreal (CA)

(73) Assignee: DGel Electrosystem Inc., Montréal, QC (CA)

( * ) Notice: Subject to any disclaimer, the term of this patent is extended or adjusted under 35 U.S.C. 154(b) by 0 days.

(21) Appl. No.: 14/562,648

(22) Filed: Dec. 5, 2014

(65) Prior Publication Data
US 2015/0185183 A1 Jul. 2, 2015

Related U.S. Application Data

(63) Continuation of application No. 13/695,005, filed as application No. PCT/CA2011/000500 on Apr. 21, 2011, now Pat. No. 9,103,779.

(60) Provisional application No. 61/440,096, filed on Feb. 7, 2011, provisional application No. 61/431,757, filed on Jan. 11, 2011, provisional application No. 61/373,315, filed on Aug. 13, 2010, provisional application No. 61/328,208, filed on Apr. 27, 2010.

(51) Int. Cl.
*G01N 27/447* (2006.01)
*B01D 57/02* (2006.01)

(52) U.S. Cl.
CPC .......... *G01N 27/44747* (2013.01); *B01D 57/02* (2013.01); *G01N 27/44704* (2013.01)

(58) Field of Classification Search
CPC ............................................... G01N 27/44747
See application file for complete search history.

(56) References Cited

U.S. PATENT DOCUMENTS

| | | | |
|---|---|---|---|
| 4,139,440 | A | 2/1979 | Chrambach et al. |
| 4,246,084 | A | 1/1981 | Gurske |
| 5,354,442 | A | 10/1994 | Allen et al. |
| 5,464,517 | A | 11/1995 | Hjerten et al. |
| 5,578,180 | A | 11/1996 | Engelhorn et al. |
| 5,922,185 | A | 7/1999 | Updyke et al. |
| 6,096,182 | A | 8/2000 | Updyke et al. |
| 6,733,647 | B2 | 5/2004 | Chan et al. |
| 2003/0121784 | A1 | 7/2003 | Updyke et al. |
| 2006/0118418 | A1 | 6/2006 | Sivaram et al. |
| 2009/0211907 | A1 | 8/2009 | Masuda et al. |
| 2011/0073478 | A1 | 3/2011 | Updyke et al. |
| 2013/0015067 | A1 | 1/2013 | Sevigny |

FOREIGN PATENT DOCUMENTS

| | | |
|---|---|---|
| JP | 2002-277438 A | 9/2002 |
| JP | 2004-509343 A | 3/2004 |
| JP | 2004-527739 A | 9/2004 |
| JP | 2009-522554 A | 6/2009 |
| WO | 03/008074 A1 | 1/2003 |
| WO | 2009027983 A1 | 3/2009 |
| WO | 2011/028535 A2 | 3/2011 |

OTHER PUBLICATIONS

BIO-RAD Safety Data Sheet for 10X Tris/CAPS Buffer, Bio-Rad Laboratories, Life Scicence Group, Jun. 18, 2015.*
"SERVA Electrophoresis Instruction Manual", 2007, 2 pages.
"SERVA Electrophoresis SDS and Native PAGE", 2010, pp. 1-11.
Basak et al., "Characterization of Buffers for Electrokinetic Separations", Applied Biochemistry and Biotechnology, vol. 44, 1994, pp. 243-261.
Gaál et al., "Electrophoresis in the separation of biological macromolecules", A Wiley-Interscience Publication, 1980, 5 pages.
GenScript, "GenScript Technical Manual No. 0210", 2008, pp. 1-9.
International Preliminary Report on Patentability received for PCT Patent Application No. PCT/CA2011/000500 completed on Jul. 4, 2012, 4 pages.
International Search Report and Written Opinion received for PCT Patent Application No. PCT/CA2011/000500 mailed on Aug. 15, 2011, 12 pages.
Peacock et al., "Molecular Weight Estimation and Separation of Ribonucleic Acid by Electrophoresis in Agarose-Acrylamide Composite Gels", Biochemistry, vol. 7 No. 2, Feb. 1968, pp. 668-674.
Peacock et al., "Resolution of Multiple Ribonucleic Acid Species by Polyacrylamide Gel Electrophoresis", Biochemistry, vol. 6, No. 6, Jun. 1967, pp. 1818-1827.
Uriel, Par Jose, "Methode Delectrophorese Dans Des Gels Dacrylamide-Agarose", Bull. Soc. Chem. Bioi. vol. 48, No. 8-9, 1966, pp. 969-982. (English Abstract Submitted).
Extended European Search Report (includes Supplementary European Search Report and Search Opinion) received for European Patent Application No. 11774241.1, mailed on Nov. 6, 2014, 6 pages.
Non-Final Office Action received for U.S. Appl. No. 13/695,005, mailed on Jul. 30, 2014, 12 pages.
Non Final Office Action received for U.S. Appl. No. 13/695,005, mailed on Dec. 24, 2014, 8 pages.
"Ready-to-Run Buffers and Solutions", Bio-Rad, Bulletin 2317 US/EG, Created Mar. 25, 2008, Retrieved from the internet on May 9, 2015.
Notice of Allowance received for U.S. Appl. No. 13/695,005, mailed on Apr. 3, 2015, 8 pages.
Office Action received for Australian Patent Application No. 2011245047, mailed on May 11, 2015, 9 pages.
Anthony K. Tan, "Increased Transfer Efficiency using a Discontinuous Buffer System with the Trans-Blot SD Semi-Dry Electrophoretic Transfer Cell", Protein Blotting, Bulletin # 2134, US/EG Rev B, 99-551 0300 Sig 031799. Created Nov. 2, 2006, Retrieved from the internet on May 8, 2015, 2 pages. <URL: http://www bio-rad com/webroot/web/pdf/Isr/literature/Bulletin 2134B pdf>.

* cited by examiner

*Primary Examiner* — J. Christopher Ball
(74) *Attorney, Agent, or Firm* — Morrison & Foerster LLP (57) ABSTRACT

There is provided an electrolyte solution for extending shelf life, and/or accelerating or improving resolution or improving transfer efficacy for blot applications, or accelerating and improving resolution, or accelerating and improving transfer efficacy of gel electrophoresis and containing Tris(hydroxymethyl)aminomethane (TRIS), at least one zwitterion, and water. The electrolyte solution may be used in buffer systems for gel electrophoresis and the preparation of gels for gel electrophoresis, such as Western blot.

16 Claims, 7 Drawing Sheets

FIG. 1A

Short polyacrylamide gel, 60 mm migration path

Migration with running buffer 1X Tris-Glycine-SDS – AIQN AGVU

Gels ran in 60 minutes

FIG. 1B

Short polyacrylamide gel, 60 mm migration path

Migration with running buffer 1X EPPS-SDS - AINN

Gels ran in 45 minutes

FIG. 1C

Short polyacrylamide gel, 60 mm migration path

Migration with running buffer 1X Glygly-SDS – AGQD AHCF

Gels ran in 60 minutes

FIG. 1D

Short polyacrylamide gel, 60 mm migration path

Migration with running buffer 1X TAPS-SDS – AIQY

Gels ran in 35 minutes

FIG. 1E

Short polyacrylamide gel, 60 mm migration path

Migration with running buffer 1X BES - AINB

Gels ran in 40 minutes

FIG. 1F

Short polyacrylamide gel, 60 mm migration path

Migration with running buffer 1X TES - AIRG

Gels ran in 40 minutes

FIG. 1G

Long polyacrylamide gel, 80 mm migration path

Migration with running buffer 1X EPPS – AELG

Gel ran in 50 minutes (Tris Glycine SDS ran in 90 minutes)

| 12% Laemmli PAGE with running buffer: Tris-Glycine-SDS, 150V, 95 min | MW (KDa) | 12% Laemmli PAGE with running buffer: Tris-EPPS-SDS, 150V, 60 min |
|---|---|---|
| | 30 | |
| | 21 | |
| | 15 | |
| | 14.3 | |

ELECTROPHORESIS BUFFER FOR FASTER MIGRATION, IMPROVED RESOLUTION AND EXTENDED SHELF-LIFE

CROSS REFERENCE TO RELATED APPLICATIONS

This is a Continuation of U.S. patent application Ser. No. 13/695,005 filed Apr. 21, 2011, which is the U.S. National Phase Patent Application of PCT/CA2011/000500, filed Apr. 21, 2011, which claims the benefit under 35 USC 119(e) to U.S. Provisional Application No. 61/440,096, filed Feb. 7, 2011, U.S. Provisional Application No. 61/431,757, filed Jan. 11, 2011, U.S. Provisional Application No. 61/373,315, filed Aug. 13, 2010, and U.S. Provisional Application No. 61/328,208, filed Apr. 27, 2010, each of which is hereby incorporated by reference in the present disclosure in its entirety.

BACKGROUND (a) Field

The subject matter disclosed generally relates to gel electrophoresis. More specifically, the subject matter disclosed relates to an electrolyte solution for accelerating or improving resolution, or accelerating and improving resolution of gel electrophoresis and containing Tris(hydroxymethyl)aminomethane (TRIS), at least one zwitterion, and water.

(b) Related Prior Art

Gel electrophoresis is a common procedure for the separation of biological molecules, such as deoxyribonucleic acid (DNA), ribonucleic acid (RNA), polypeptides and proteins. In gel electrophoresis, the molecules are separated into bands according to the rate at which an imposed electric field causes them to migrate through a filtering gel.

The basic apparatus used in this technique consists of a gel enclosed in a glass tube, sandwiched as a slab between glass or plastic plates, or poured in a plastic tray. The gel has an open molecular network structure, defining pores which are saturated with an electrically conductive buffered solution. These pores through the gel are large enough to admit passage of the migrating macromolecules.

The gel is placed in a chamber in contact with buffer solutions which make electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel.

The most common buffer system employed for the separation of proteins is the Laemmli buffer system consists of 0.375 M tris(hydroxy methyl)amino-methane (Tris), titrated to pH 8.8, with HCl, in the separating gel. The stacking gel consists of 0.125 M Tris, titrated to pH 6.8. The anode and cathode running buffers contain 0.024 M Tris, 0.192 M glycine, 0.1% SDS. Many different gel separation materials have been disclosed, with different compositions, pH characteristics, voltage requirements, etc. The goal of most of the recent innovations in the field has been to provide an electrophoresis gel which can be used to perform a faster, more accurate, more stable, or therefore more versatile electrophoresis.

A number of different gel buffer systems have been proposed for use at or around neutral pH that do not involve the use of the Tris-HCl Glycine buffer system of Laemmli.

For example, U.S. Pat. No. 6,096,182 to Updyke et al. discloses an electrophoresis gel at a neutral pH. The advantage of producing such a gel is that the gel system is stable, with reduced reactivity and increased shelf life.

U.S. Pat. No. 5,464,517 to Hjerten et al. discloses an electrophoresis buffer which has a high buffering capacity and low electrical conductivity. The advantage of this type of buffer, particularly in capillary electrophoresis, is that it allows the separation to be performed at a higher voltage and consequently more quickly.

A majority of innovations have focused on improving electrophoresis by proposing new recipes for the gel buffer.

Therefore, there is a need for reagents that will improve the speed at which electrophoresis can be performed, improve gel resolution, as well as increase the shelf life of gels.

SUMMARY

In a first embodiment there is disclosed an electrolyte solution for accelerating, or improving resolution, or improving transfer efficacy for blot applications, including Western blot for example, or accelerating and improving resolution, or accelerating and improving Western transfer efficacy of gel electrophoresis containing:

Tris(hydroxymethyl)aminomethane (TRIS);

at least one zwitterion that may be chosen from 2-amino-2methyl-1,3-propanediol (AMPD), N,N-bis[2-hydroxyethyl]-2-aminoethanesulphonic acid (BES), N-Glycylglycine (Gly-Gly), 4-(2-hydroxyethyl)piperazine-1-propanesulfonic acid (EPPS or HEPPS), and 3-(cyclohexylamino)-2-hydroxy-1-propanesulfonic acid (CAPSO), N-(1,1-Dimethyl-2-hydroxyethyl)-3-amino-2-hydroxypropanesulfonic acid (AMPSO), 3-(cyclohexylamino)-1-propanesulfonic acid (CAPS), 2-(cyclohexylamino)ethanesulfonic acid (CHES), 3-[N-Bis(hydroxyethyl)amino]-2-hydroxypropanesulfonic acid (DIPSO), N-(2-Hydroxyethyl)piperazine-N'-(4-butanesulfonic acid) (HEPBS), 4-(N-Morpholino)butanesulfonic acid (MOBS), 3-N-Morpholino propanesulfonic acid (POPSO), N-Tris(hydroxymethyl)methyl-4-aminobutanesulfonic acid (TABS), N-Tris(hydroxymethyl)methyl-3-aminopropanesulfonic acid (TAPS), (2-[2-hydroxy-1,1-bis(hydroxymethyl)ethylamino]ethanesulphonic acid) (TES)), (2-[2-acetamino]-2-aminoethanesulphonic acid) (ACES), (1,4-piperazinediethanesulphonic acid) (PIPES), (3-[N-morpholino]propancsulphonic acid)(MOPS), and Piperazine-N,N'-bis(3-propanesulfonic Acid) (PIPPS); and water.

The TRIS component of the above electrolyte solution may be selected from the group consisting of: Tris-HCl Glycine, Tris-Glycine, MOPS-Bis-Tris, EPPS-Tris-SDS, and the like.

The zwitterion may be chosen from N,N-bis[2-hydroxyethyl]-2-aminoethanesulphonic acid (BES), 3-(cyclohexylamino)-1-propanesulfonic acid (CAPS), 2-(cyclohexylamino)ethanesulfonic acid (CHES), N-Glycylglycine (Gly-Gly), 4-(2-hydroxyethyl)piperazine-1-propanesulfonic acid (EPPS or HEPPS), (2-[2-hydroxy-1,1-bis(hydroxymethyl)ethylamino]ethanesulphonic acid) (TES)), (2-[2-acetamino]-2-aminoethanesulphonic acid) (ACES), (1,4-piperazinediethanesulphonic acid) (PIPES), (3-[N-morpholino]propancsulphonic acid)(MOPS), and N-Tris(hydroxymethyl)methyl-3-aminopropanesulfonic acid (TAPS) for accelerating gel electrophoresis.

The zwitterion may be chosen from N-(1,1-Dimethyl-2-hydroxyethyl)-3-amino-2-hydroxypropanesulfonic acid (AMPSO), 3-(cyclohexylamino)-2-hydroxy-1-propanesulfonic acid (CAPSO), N,N-bis[2-hydroxyethyl]-2-aminoethanesulphonic acid (BES), N-Glycylglycine (Gly-Gly), 4-(2-hydroxyethyl)piperazine-1-propanesulfonic acid (EPPS or HEPPS), (2-[2-hydroxy-1,1-bis(hydroxymethyl)ethylamino]ethanesulphonic acid) (TES), (2-[2-acetamino]-2-aminoethanesulphonic acid) (ACES), (1,4-piperazinediethanesulphonic acid) (PIPES), (3-[N-morpholino]propanesulphonic acid)(MOPS), and N-Tris(hydroxymethyl)methyl-3-aminopropanesulfonic acid (TAPS) for improving resolution of gel electrophoresis.

The zwitterion may be chosen from N-Glycylglycine (Gly-Gly), 4-(2-hydroxyethyl)piperazine-1-propanesulfonic acid (EPPS or HEPPS),), N,N-bis[2-hydroxyethyl]-2-aminoethanesulphonic acid (BES), (2-[2-hydroxy-1,1-bis(hydroxymethyl)ethylamino]ethanesulphonic acid) (TES), (2-[2-acetamino]-2-aminoethanesulphonic acid) (ACES), (1,4-piperazinediethanesulphonic acid) (PIPES), (3-[N-morpholino]propanesulphonic acid)(MOPS), and N-Tris(hydroxymethyl)methyl-3-aminopropanesulfonic acid (TAPS) for, accelerating and improving resolution of gel electrophoresis The zwitterion may be chosen from N-Glycylglycine (Gly-Gly), 4-(2-hydroxyethyl)piperazine-1-propanesulfonic acid (EPPS or HEPPS), N,N-bis[2-hydroxyethyl]-2-aminoethanesulphonic acid (BES), and 3-(cyclohexylamino)-2-hydroxy-1-propanesulfonic acid (CAPSO) for accelerating and improving Western transfer efficacy of gel electrophoresis.

The zwitterions may be chosen from N-Glycylglycine (Gly-Gly), 4-(2-hydroxyethyl)piperazine-1-propanesulfonic acid (EPPS or HEPPS), N,N-bis[2-hydroxyethyl]-2-aminoethanesulphonic acid (BES), and 3-(cyclohexylamino)-2-hydroxy-1-propanesulfonic acid (CAPSO) can also be used in combination with one or more other zwitterions from the group 2-amino-2methyl-1,3-propanediol (AMPD), N-(1,1-Dimethyl-2-hydroxyethyl)-3-amino-2-hydroxypropanesulfonic acid (AMPSO), 3-(cyclohexylamino)-1-propanesulfonic acid (CAPS), 2-(cyclohexylamino)ethanesulfonic acid (CHES), 3-[N-Bis(hydroxyethyl)amino]-2-hydroxypropanesulfonic acid (DIPSO), N-(2-Hydroxyethyl)piperazine-N'-(4-butanesulfonic acid) (HEPBS), 4-(N-Morpholino)butanesulfonic acid (MOBS), 3-N-Morpholino propanesulfonic acid (POPSO), N-Tris(hydroxymethyl)methyl-4-aminobutanesulfonic acid (TABS), N-Tris(hydroxymethyl)methyl-3-aminopropanesulfonic acid (TAPS), (2-[2-hydroxy-1,1-bis(hydroxymethyl)ethylamino]ethanesulphonic acid) (TES) and Piperazine-N,N'-bis(3-propanesulfonic Acid) (PIPPS) and keep its accelerating efficacy in electrophoresis separation and Western transfer as well as providing improved separation resolution.

The zwitterions for improving resolution may be 4-(2-hydroxyethyl)piperazine-1-propanesulfonic acid (EPPS or HEPPS).

The electrolyte solution may have a pH from about 8.0 to about 8.8.

The electrolyte solution may comprise methanol, up to 20%.

The electrolyte solution may comprise sodium dodecyl sulphate (SDS) or lithium dodecyl sulfate (LDS), up to 5%.

The electrolyte solution may comprise a chelating agent having the name: ethylenediaminetetraacetate (EDTA), ethylene glycol tetraacetic acid (EGTA), trisodium nitrilotriacetate, hydroxyethyl ethylenediamine trisodium acetate (trisodium HEDTA), diethylene triamino pentasodium acetate or uramil disodium acetate.

The concentration of Tris(hydroxymethyl)aminomethane (TRIS) may be from about 10 mM to about 500 mM, from about 50 mM to about 150 mM, or from about 50 mM to about 250 mM, or may be 150 mM.

The concentration of the zwitterion may be from about 1 mM to 500 mM, from about 10 mM to about 500 mM, or from about 25 mM to about 50 mM, or from about 50 mM to about 100 mM, or may be 50 mM or may be 100 mM.

The concentration of sodium dodecyl sulphate (SDS) may be 0.5% (wt/vol) or less, or may be 0.1% (wt/vol) or less, or may be 0.1% (wt/vol).

The concentration of ethylenediaminetetraacetate (EDTA) may be 0.5% (wt/vol) or less, or may be 0.05% (wt/vol) or less or may be 0.03% (wt/vol).

The zwitterions may be a combination of 4-(2-hydroxyethyl)piperazine-1-propanesulfonic acid (EPPS or HEPPS), (2-[2-acetamino]-2-aminoethanesulphonic acid) (ACES), (1,4-piperazinediethanesulphonic acid) (PIPES), and (3-[N-morpholino]propanesulphonic acid)(MOPS).

In a second embodiment, there is disclosed an electrophoresis gel comprising the electrolyte solution according to the present invention. The gel may be an acrylamide gel, and the concentration of acrylamide may be from about 4% (wt/vol) to about 25% (wt/vol). The gel may be an agarose gel, and the concentration of agarose may be from about 0.5% (wt/vol) to about 3% (wt/vol). The gel may be an acrylamide and agarose gel, and the concentration of acrylamide may be from about less than 1% (wt/vol) to about 25% (wt/vol) and the concentration of agarose may be from about 0.5% (wt/vol) to about 3% (wt/vol). The electrophoresis gel may comprise sodium dodecyl sulphate (SDS).

The zwitterion may be chosen from 2-amino-2methyl-1,3-propanediol (AMPD), N-(1,1-Dimethyl-2-hydroxyethyl)-3-ami no-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethypethylamino]ethanesulphonic acid) (TES), N-Tris(hydroxymethyl)methyl-3-aminopropanesulfonic acid (TAPS) and 3-N-Morpholino propanesulfonic acid (POPSO) for improving shelf life of the gel.

The pH of the gel may be from about 8.0 to about 8.8.

In yet another embodiment, there is disclosed a method of accelerating or improving the resolution, or accelerating and improving the resolution of the electrophoretic separation of at least one sample comprising the step of applying a voltage to an electrolyte solution according to the present invention, in contact with an electrophoresis gel containing the at least one sample therein.

The electrophoresis gel is a gel according to the present invention.

In yet another embodiment, there is disclosed a method of accelerating or improving the resolution of, or improving transfer efficacy, or accelerating and improving the resolution, or accelerating and improving transfer efficacy of the electrophoretic separation of at least one sample comprising the step of applying a voltage to an electrolyte solution adapted to perform gel electrophoresis in contact with an electrophoresis gel according to the present invention containing the at least one sample therein.

In yet another embodiment, there is disclosed a method for improving resolution of an electrophoretic separation of at least one sample comprising adding at least one zwitterion chosen from 2-amino-2methyl-1,3-propanediol (AMPD), N,N-bis[2-hydroxyethyl]-2-aminoethanesulphonic acid (BES), N-Glycylglycine (Gly-Gly), 4-(2-hydroxyethyl)piperazine-1-propanesulfonic acid (EPPS or HEPPS), and 3-(cyclohexylamino)-2-hydroxy-1-propanesulfonic acid (CAPSO), N-(1,1-Dimethyl-2-hydroxyethyl)-3-amino-2-hydroxypropanesulfonic acid (AMPSO), 3-(cyclohexylamino)-1-propanesulfonic acid (CAPS), 2-(cyclohexylamino)ethanesulfonic acid (CHES), 3-[N-Bis (hydroxyethyl)amino]-2-hydroxypropanesulfonic acid (DIPSO), N-(2-Hydroxyethyl)piperazine-N'-(4-butanesulfonic acid) (HEPBS), 4-(N-Morpholino)butanesulfonic acid (MOBS), 3-N-Morpholino propanesulfonic acid (POPSO), N-Tris(hydroxymethyl)methyl-4-aminobutanesulfonic acid (TABS), N-Tris(hydroxymethyl)methyl-3-aminopropanesulfonic acid (TAPS), (2-[2-hydroxy-1,1-bis(hydroxymethypethylamino]ethanesulphonic acid) (TES), (2-[2-acetamino]-2-aminoethanesulphonic acid) (ACES), (1,4-piperazinediethanesulphonic acid) (PIPES), (3-[N-morpholino]propancsulphonic acid)(MOPS), and Piperazine-N,N'-bis(3-propanesulfonic Acid) (PIPPS) to an electrophoresis buffer or to an electrophoresis gel, or to both an electrophoresis buffer and an electrophoresis gel. The zwitterion may be 4-(2-hydroxyethyl)piperazine-1-propanesulfonic acid (EPPS or HEPPS).

In yet another embodiment, there is disclosed a use of an electrolyte solution according to the present invention for accelerating gel electrophoresis.

In yet another embodiment, there is disclosed a use of an electrolyte solution according to the present invention for improving resolution of gel electrophoresis.

In yet another embodiment, there is disclosed a use of an electrolyte solution according to the present invention for accelerating and improving resolution of gel electrophoresis.

In yet another embodiment, there is disclosed a use of a gel according to the present invention for accelerating or improving resolution, or accelerating and improving resolution of gel electrophoresis.

In yet another embodiment, there is disclosed a use of an electrolyte solution according to the present invention for the preparation of an electrophoresis gel, wherein the zwitterions is a compound of formula: 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis (hydroxymethypethylamino]ethanesulphonic acid) (TES), N-Tris(hydroxymethyl)methyl-3-aminopropanesulfonic acid (TAPS) or 3-N-Morpholino propanesulfonic acid (POPSO) for improving shelf life of a gel.

The following terms are defined below.

The term "improved resolution" is intended to mean a better resolution which allows separation of sharper or narrower bands of molecules, distanced or spaced apart from each other as opposed to other means of separation which have broader or thicker bands. This facilitates physical separation or molecular weight identification of the different molecules that make up these bands over the entire range of molecular weight.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

FIG. 7 (A-C) illustrates a comparison of the migration resolution of 10% acrylamide Tris-glycine based gel (A), 4-20% acrylamide Tris-glycine based gel (B), and 10% acrylamide EPPS based gel, in an electrolyte solutions according to the present invention.

DETAILED DESCRIPTION OF THE PREFERRED EMBODIMENTS

The present inventors have now surprisingly found that selecting specific zwitterions to prepare an electrolyte solution for use in gel electrophoresis can result in unexpected increase in electrophoresis speed, improvement in gel resolution, or both. These improvements may be observed when the electrolyte solutions are used as running buffer (also referred to as "reservoir" buffer) for the electrophoresis apparatus, as well as when used in as buffer system for the preparation of the electrophoresis gels (i.e. in the gel). Furthermore, when used in the preparation of electrophoresis gels, some of these zwitterions will also increase in the shelf life of gels prepared using these electrolyte solutions.

In embodiments there are disclosed an electrolyte solution for performing gel electrophoresis. The electrolyte contains specific components.

Zwitterions

A zwitterion is a chemical compound that carries a total net charge of 0 and is thus electrically neutral, but carries formal charges on different atoms. Zwitterions are polar and are usually very water-soluble, but poorly soluble in most organic solvents. Zwitterions will exist mostly as zwitterions in a certain range of pH. The pH at which the average charge is zero is known as the molecule's isoelectric point.

The zwitterions of interest in the present invention belong to the category commonly referred to as biological buffers, which are buffers that are commonly used as buffering agents in biological laboratories. Examples of biological buffers that can be cited are those known as bis-TRIS (2-bis[2-hydroxyethyl]amino-2-hydroxymethyl-1,3-propanediol), ADA (N-[2-acetamido]-2-iminodiacetic acid), ACES (2-[2-acetamino[-2-aminoethanesulphonic acid), PIPES (1,4-piperazinediethanesulphonic acid), MOPSO (3-[N-morpholino]-2-hydroxypropanesulphonic acid), bis-TRIS PROPANE (1,3-bis[tris(hydroxymethyl)methylaminopropane]), BES (N,N-bis[2-hydroxyethyl]-2-aminoethanesulphonic acid), MOPS (3-[N-morpholino]propancsulphonic acid), TES (2-[2-hydroxy-1,1-bis(hydroxymethyl)ethylamino]ethanesulphonic acid), HEPES (N-[2-hydroxyethyl]piperazine-N'-(2-ethanesulphonic)acid), DIPSO (3-N,N-bis[2-hydroxyethyl]amino-2-hydroxypropanesulphonic acid), MOBS (4-N-morpholinobutanesulphouic acid), TAPSO (3[N-tris-hydroxymethyl-methylamino]-2-hydroxypropanesulphonic acid), TRIS (2-amino-24hydroxymethyl]-1,3-propanediol), HEPPSO (N-[2-hydroxyethyl]piperazine-N'-[2-hydroxypropanesulphonic]acid), POPSO (piperazie-N,N'-bis[2-hydroxypropanesulphonic]acid), TEA (triethanolamine), EPPS (or HEPPS) (N-[2-hydroxyethyl]-piperazine-N'-[3-propanesulphonic]acid), TRICINE (N-tris[hydroxymethyl]methylglycine), GLY-GLY (diglycine), BICINE (N,N-bis[2-hydroxyethyl]glycine), HEPBS (N-[2-hyd roxyethyl]piperazine-N'-[4-butanesulphonic]acid), TAPS (N-tris[hydroxymethyl]methyl-3-aminopropanesulphonic acid), AMPD (2-amino-2-methyl-1,3-propanediol), TABS (N-tris[hydroxymethyl]methyl-4-aminobutanesulphonic acid), AMPSO (3-[(1,1-dimethyl-2-hydroxyethyl)amino]-2-hydroxypropanesulphonic acid), CHES (2-(N-cyclohexylamino)ethanesulphonic acid), CAPSO (3-[cyclohexylamino]-2-hydroxy-1-propanesulphonic acid), AMP (2-amino-2-methyl-1-propanol), CAPS (3-cyclohexylamino-1-propanesulphonic acid), and CABS (4-[cyclohexylamino]-1-butanesulphonic acid).

Although the biological buffering property of these zwitterions has been recognized, the capacity of a select group of these zwitterions to positively impact the performance of gel electrophoresis, and the shelf life of gels for gel electrophoresis was not.

Preferably the zwitterions include ACES (2-[2-acetamino[-2-aminoethanesulphonic acid), PIPES (1,4-piperazinediethanesulphonic acid), MOPS (3-[N-morpholino]propancsulphonic acid), 2-amino-2methyl-1,3-propanediol (AMPD), N-Glycylglycine (Gly-Gly), 4-(2-hydroxyethyl)piperazine-1-propanesulfonic acid (EPPS or HEPPS), and 3-(cyclohexylamino)-2-hydroxy-1-propanesulfonic acid (CAPSO), N-(1,1-Dimethyl-2-hydroxyethyl)-3-amino-2-hydroxypropanesulfonic acid (AMPSO), 3-(cyclohexylamino)-1-propanesulfonic acid (CAPS), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino]ethanesulphonic acid) (TES), 3-[N-Bis(hydroxyethyl)amino]-2-hydroxypropanesulfonic acid (DIPSO), 4-(2-Hydroxyethyl)piperazine-1-propanesulfonic acid (EPPS or HEPPS), N-Glycylglycine (Gly-Gly), N-(2-Hydroxyethyl)piperazine-N'-(4-butanesulfonic acid) (HEPBS), 4-(N-Morpholino)butanesulfonic acid (MOBS), 3-N-Morpholino propanesulfonic acid (POPSO), N-Tris(hydroxymethyl)methyl-4-aminobutanesulfonic acid (TABS), N-Tris(hydroxymethyl)methyl-3-aminopropanesulfonic acid (TAPS) and Piperazine-N,N'-bis(3-propanesulfonic Acid) (PIPPS). These zwitterions significantly improve the speed at which electrophoresis may be performed, improve gel resolution, or both. The zwitterions may improve resolution by improving the definition (or sharpness), by providing thinner or narrow bands) of the molecules separated, by improving the separation between the molecules (i.e. the distance between the individual bands, or by both improving the definition (or sharpness) and separation of the molecules. Also, when used for the preparation of gels, increase in the shelf life of gels prepared using these electrolyte solutions.

The ranges of concentration over which these zwitterions may be used for the preparation of electrolyte solutions according to the present invention, for accelerating gel electrophoresis and/or improving gel resolution discussed herein are from about 1 mM to about 500 mM, or from about 10 mM to about 500 mM, or from about 25 mM to about 50 mM, or from about 25 mM to about 100 mM, or from about 10 mM to about 100 mM, or from about 1 mM to about 100 mM, or from about 1 mM to about 75 mM, or from about 10 mM to about 75 mM, or from about 1 mM to about 10 mM, or from about 1 mM to about 50 mM or from about 10 mM to about 50 mM.

The ranges of concentration over which these zwitterions may be used for improving the shelf life of gels prepared according to the present invention are from about 1 mM to about 500 mM, or from about 10 mM to about 500 mM, or from about 10 mM to about 100 mM, or from about 1 mM to about 100 mM, or from about 1 mM to about 75 mM, or from about 10 mM to about 75 mM, or from about 1 mM to about 10 mM, or from about 1 mM to about 50 mM or from about or from about about 10 mM to about 50 mM or, from about 25 mM to about 375 mM, and preferably, at 100 mM.

Preferably, the zwitterions to accelerate gel electrophoresis (as compared to the classical Tris-Glycine-SDS at pH 8.3 of Laemmli) are 2-amino-2methyl-1,3-propanediol (AMPD), N, N-bis[2-hydroxyethyl]-2-aminoethanesulphonic acid (BES), 3-(cyclohexylamino)-1-propanesulfonic acid (CAPS), 2-(cyclohexylamino)ethanesulfonic acid (CHES), N-Glycylglycine (Gly-Gly), 4-(2-hydroxyethyl)piperazine-1-propanesulfonic acid (EPPS or HEPPS), N-Tris(hydroxymethyl)methyl-3-aminopropanesulfonic acid (TAPS), ACES (2-[2-acetamino[-2-aminoethanesulphonic acid), PIPES (1,4-piperazinediethanesulphonic acid), MOPS (3-[N-morpholino]propancsulphonic acid), and (2-[2-hydroxy-1,1-bis(hydroxymethypethylamino]ethanesulphonic acid) (TES). When using the above zwitterions in the electrolyte solutions according to the present invention, for running and/or preparing an electrophoresis gel, the migration speed of gels may be increase by about 30% or more. The zwitterions may be used alone or in combination.

Optimal results with 4-(2-hydroxyethyl)piperazine-1-propanesulfonic acid (EPPS or HEPPS) are obtained at pH of about pH 8.0 to 8.8.

Preferably the zwitterions to improve the resolution of gels during electrophoresis (as compared to the classical Tris-Glycine-SDS at pH 8.3 of Laemmli) are N-(1,1-Dimethyl-2-hydroxyethyl)-3-amino-2-hydroxypropanesulfonic acid (AMPSO), N, N-bis[2-hydroxyethyl]-2-aminoethanesulphonic acid (BES), N-Glycylglycine (Gly-Gly), 4-(2-hydroxyethyl)piperazine-1-propanesulfonic acid (EPPS or HEPPS), 3-N-Morpholino propanesulfonic acid (POPSO) ACES (2-[2-acetamino[-2-aminoethanesulphonic acid), PIPES (1,4-piperazinediethanesulphonic acid), MOPS (3-[N-morpholino]propancsulphonic acid), and N-Tris(hydroxymethyl)methyl-3-aminopropanesulfonic acid (TAPS). When using the above zwitterions in the electrolyte solutions according to the present invention, for running and/or preparing an electrophoresis gel, the resolution of the gels may be increase by 40% or more. Most preferably the zwitterion to improve the resolution of gels during electrophoresis is 4-(2-hydroxyethyl)piperazine-1-propanesulfonic acid (EPPS or HEPPS). The resolution may be improved by improving the definition (or sharpness), by providing thinner or narrow bands) of the molecules separated, by improving the separation between the molecules (i.e. the distance between the individual bands, or by both improving the definition (or sharpness) and separation of the molecules. According to one embodiment of the present invention, the improvement in resolution may result in a normal, continuous acrylamide concentration gel showing characteristic similar to a gradient concentration of acrylamide gel. These gradient-like improvements in resolution offer better and greater separation between bands of molecules, while maintaining or improving sharpness of the protein bands.

Preferably, the zwitterions to accelerate gel electrophoresis and to improve the resolution of gels during electrophoresis (as compared to the classical Tris-Glycine-SDS at pH 8.3 of Laemmli) are N,N-bis[2-hydroxyethyl]-2-aminoethanesulphonic acid (BES), N-Glycylglycine (Gly-Gly), N-Tris(hydroxymethyl)methyl-3-aminopropanesulfonic acid (TAPS), ACES (2-[2-acetamino[-2-aminoethanesulphonic acid), PIPES (1,4-piperazinediethanesulphonic acid), MOPS (3-[N-morpholino]propanesulphonic acid), and 4-(2-hydroxyethyl)piperazine-1-propanesulfonic acid (EPPS or HEPPS). When using the above zwitterions in the electrolyte solutions according to the present invention, for running and/or preparing an electrophoresis gel, the resolution of the gels may be increase by 40% or more and the migration speed of gels may be increase by about 30% or more. Most preferably the zwitterion to accelerate gel electrophoresis and to improve the resolution of gels during electrophoresis is 4-(2-hydroxyethyl)piperazine-1-propanesulfonic acid (EPPS or HEPPS). The resolution may be improved by improving the definition (or sharpness), by providing thinner or narrow bands) of the molecules separated, by improving the separation between the molecules (i.e. the distance between the individual bands, or by both improving the definition (or sharpness) and separation of the molecules.

Preferably the zwitterions to improve the shelf life of gels (as compared to the classical Tris-Glycine-SDS gels of Laemmli) are 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 2-(cyclohexylamino)ethanesulfonic acid (CHES), and 3-N-Morpholino propanesulfonic acid (POPSO).

Optimal results with 4-(2-hydroxyethyl)piperazine-1-propanesulfonic acid (EPPS or HEPPS) are obtained at pH of about pH 8.0 to 8.8.

Tris(hydroxymethyl)aminomethane Base (TRIS)

Tris is an abbreviation of the organic compound known as tris(hydroxymethyl)aminomethane, with the formula $(HOCH_2)_3CNH_2$. Tris is extensively used in biochemistry and molecular biology. In biochemistry, Tris is widely used as a component of buffer solutions, such as in TAE and TBE buffer, especially for solutions of nucleic acids.

Tris also allows the pH of the electrolyte solution of the present invention to be set towards more basic pH values. Tris also has a positive impact on the migration speed in the preferred concentration ranges.

The ranges of concentration over which Tris base may be used for the preparation of electrolyte solutions according to the present invention, for accelerating gel electrophoresis and improving gel resolution as discussed herein are from about 10 mM to about 500 mM. The Tris concentration has a direct impact on the pH of the solution. An increasing amount of Tris increases the pH. This allow fine adjustments in adapting the electrolyte solution of the present invention to different gel chemistry and keeping a proper pH ratio compatible with gel and buffer. Preferably the concentration of Tris is from about 50 mM to about 150 mM, or from about 50 mM to about 250 mM and most preferably, at about 150 mM.

The ranges of concentration over which Tris base may be used for improving the shelf life of gels prepared according to the present invention is from about 50 mM to about 375 mM, and preferably 150 mM.

Sodium Dodecyl Sulfate or Other Anionic Surfactants

Sodium dodecyl sulfate (SDS) $(C_{12}H_{25}SO_4Na)$ is an anionic surfactant is commonly used in preparing proteins for electrophoresis in the SDS-PAGE technique. The molecule has a tail of 12 carbon atoms, attached to a sulfate group, giving the molecule the amphiphilic properties required of a detergent.

SDS may be optionally added to the electrolyte solution of the present invention. The superior results obtained with the electrolyte solutions according to the present invention are obtained independently of the presence of SDS. The ranges of concentration over which SDS may be used for the preparation of electrolyte solutions according to the present invention, for all the applications discussed herein are from 0.5% or less. Preferably, from about 0.1% or less, and most preferably, at 0.1%.

Other anionic surfactants may be included in the electrolyte solution of the present invention, such as, in a non-limiting manner facultative, one anionic surfactant to provide to the buffer denaturing properties for protein analysis: SDS, sodium dodecyl sulphate, sodium lauryl sulfate (SLS), sodium laurilsulfate or sodium, NaDS. The ranges of concentration over which they may be used for the preparation of electrolyte solutions according to the present invention, for all the applications discussed herein are from 1.0% or less. Preferably, from about 0.1% or less, and most preferably, at about 0.1%.

Chelating Agents

Ethylenediaminetetraacetate (EDTA) has a role as a chelating agent, i.e. its ability to "sequester" metal ions such as $Ca^{2+}$ and $Fe^{3+}$. After being bound by EDTA, metal ions remain in solution but exhibit diminished reactivity. Other chelating agents may include ethylene glycol tetraacetic acid (EGTA), trisodium nitrilotriacetate, hydroxyethyl ethylenediamine trisodium acetate (trisodium HEDTA), diethylene triamino pentasodium acetate or uramil disodium acetate.

EDTA may be optionally added to the electrolyte solution of the present invention. The ranges of concentration over which EDTA may be used for the preparation of electrolyte solutions according to the present invention, for all the applications discussed herein are from 0.5% or less. Preferably, from about 0.05% or less, and most preferably, at 0.03%.

Methanol

In electrophoresis for transfer onto membranes, methanol is normally added to the transfer buffer to slow the protein migration and normally permit a more equal protein transfer between the high molecular weight proteins and the low molecular weight. In standard protocol, it is used as 10% or 20% of methanol. The efficacy of fast transfer with electrolyte solutions according to the present invention containing 0% to 20% methanol is working equally well to 100% efficacy in transfer under all these conditions.

Use of the Electrolyte Solutions

In use the electrolyte solutions of the present invention is compatible with a very wide range of other buffer systems. The electrolyte solution of the present invention may be used to run electrophoresis of gels of any type, prepared with the same or with different buffer systems than that of the present invention, even including gels using different chemistries, such as MOPS as a buffer (such as those described in US Patent publication No. 20060118418), under the appropriate conditions.

According to one embodiment, electrolyte solution according to the present invention containing Tris and the zwitterions EPPS (e.g. from about 10 mM to about 100 mM), ACES (e.g. from about 10 mM to about 75 mM), MOPS (e.g. from about 10 mM to about 50 mM) and PIPES (e.g. from about 1 mM to about 10 mM) may be used to improve resolution and migration speed of gels based on different chemistries than Leammli's. An anionic surfactant (such as SDS from about 0% to about 1%) may be included in such buffers to provide denaturing properties. The resolution may be improved by improving the definition (or sharpness), by providing thinner or narrow bands) of the molecules separated, by improving the separation between the molecules (i.e. the distance between the individual bands, or by both improving the definition (or sharpness) and separation of the molecules.

According to the present invention, electrophoresis includes the separation of samples of DNA or protein or any other type of molecule that may be separated accordingly, as well as their transfer onto membranes or other suitable solid support such has nitrocellulose, nylon, PVDF or other types of membranes that are commonly used for applications such as Western transfer and blotting.

The electrolyte solution according to the present invention may be used in transfer systems of commercial make (e.g. wet, semi-dry or dry transfer systems). For examples, the electrolyte solution according to the present invention may be employed in semi-dry or dry transfer systems such as Invitrogen XCell II™ Blot Module, Pierce™ Fast Western System, Bio-Rad's Trans-Blot SD™ Semi-Dry Electrophoretic Transfer Cell and equivalent equipment. Liquid (i.e. wet) systems such as Bio-Rad Mini Trans-Blot® Module, GE MiniVe Blot module and other equivalents. Electrophoresis systems such as the eSTain™ Protein Staining System from GenScript, which comprise both the electrophoresis unit and the power supply may also work with the electrolyte solution according to the present invention. Other equivalent systems also functions as well.

The electrolyte solution of the present invention may be used as the buffer system in most of gels used in molecular biology and biochemistry, as described in classical references such as: Uriel 1966, Bull. Soc. Chem. Biol. 48:969; Peacock & Dingman 1967, Biochem 6(6), 1818-1827; Peacock & Dingman 1968, Biochem 7(2), 668-674; Gaal, Electrophoresis in the separation of biological macromolecules, p 422, Wiley, 1980. The electrolyte solutions of the present invention may be included in acrylamide gels (polyacrylamide gels), under native (without SDS) or denaturing conditions (with SDS) that are typically prepared with acrylamide concentrations from about 4% to about 25%. The electrolyte solutions of the present invention may be included in agarose gels that are typically prepared with agarose concentrations from about 0.5% to about 3%.

EPPS (or HEPPS), TAPS, TES, BES or Glygly can be added to the Laemmli buffer Tris-Glycine-SDS at a working concentration of 25 mM to 150 mM and preferably at 50 mM and accelerate the migration efficacy of the Laemmli buffer by about 30%. In electrophoresis for transfer onto membranes, methanol is normally added to the transfer buffer to slow the protein migration and normally permit a more equal protein transfer between the high molecular weight proteins and the low molecular weight. In standard protocol, it is used as 10% or 20% of methanol. The efficacy of fast transfer with electrolyte solutions according to the present invention containing 0% to 20% methanol is working equally well to 100% efficacy in transfer under all these conditions.

Alternative Embodiments

EXAMPLE 1

Exemplary electrolyte solutions compositions were prepared to be used with polyacrylamide or agarose gels made using classic recipes such as the Laemmli buffer system (Tris-Glycine-SDS). The exemplary electrolyte solutions were prepared and tested using a common basic recipe:

Zwitterions, 50 mM, Tris (Base), 100 mM, SDS 0.1%, and EDTA 0.03%. For each prepared solution, the pH is measured, and if the value was outside of the pH 7.9 to 8.6 range, it was adjusted with HCl to acidify, or NaOH to make more basic.

500 ml of running buffer were prepared for each zwitterions, and run against a precast IDGel™ (made with Tris pH 8.3 as buffering solution). After the electrophoretic run, the migration speed for the migration front to reach the bottom of the gel, and the resolution of a prestained molecular weight marker containing 10 bands weighing between 15 KDa to 175 KDa was measured. The resolution of each of these bands has been compared to a control IDGel™ ran with the standard Laemmli running buffer (Tris-Glycine-SDS). The results we obtained are as follows in table 1.

TABLE I

| Zwitterion | Gel size (migration length) | Running time | Resolution |
| --- | --- | --- | --- |
| AMPD | 60 mm | 45 min | ++ |
| AMPSO | 60 mm | 50 min | +++ |
| BES | 60 mm | 40 min | ++(+) |
| CAPS | 60 mm | 40 min | ++ |
| CAPSO | 60 mm | 60 min | (+++) |
| CHES | 60 mm | 42 min | +(+) |
| EPPS (or HEPPS) | 60 mm | 45 min | +++ |
| Glygly | 60 mm | 45 min | ++(+) |
| POPSO | 60 mm | 50 min | ++ |
| TAPS | 60 mm | 35 min | +++ |
| TES | 60 mm | 40 min | +++ |
| TGS* | 60 mm | 60 min | ++ |

*Tris-Glycine-SDS = baseline

The resolution is compared by measuring the thickness of proteins bands of 30 KDa, 21 KDA, 15 KDA and 14.3 KDa after migration in the test gel. A reduction of the band thickness by at least 50% will be noted as a "+++" sign. Thicker protein bands, indicative of lower resolution, is shown with less "+" signs. The baseline is "++", which is the result obtained by a Tris-Glycine-SDS gel, and a lesser number of "+" signs indicate thicker bands than baseline, and therefore worst average resolution.

Figure 1A:
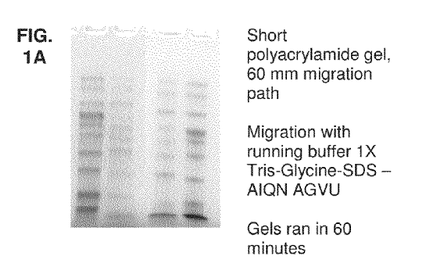
FIG. 1A- FIG. 1G illustrate polyacrylamide gels electrophoresed in electrolyte solutions according embodiments of the present invention and compared to a gel electrophoresed on Tris-glycine-SOS (baseline) solution.
Figure 1B:
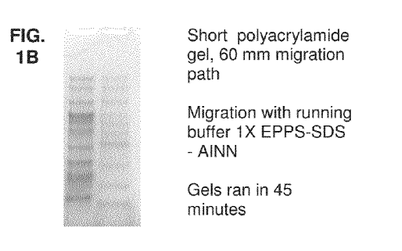
Figure 1C:
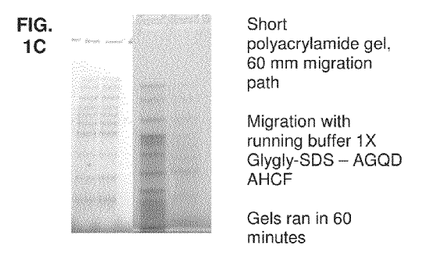
Figure 1D:
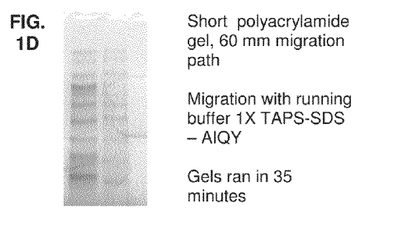
Figure 1E:
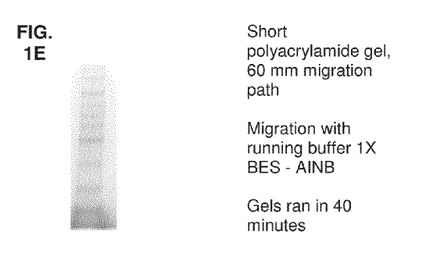
Figure 1F:
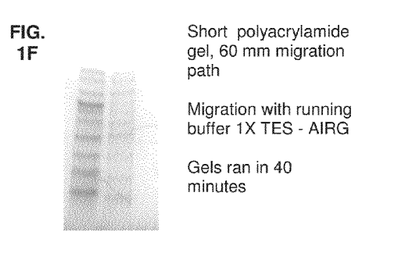
Figure 1G:
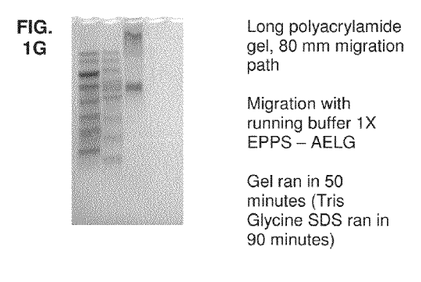
Figure 2:
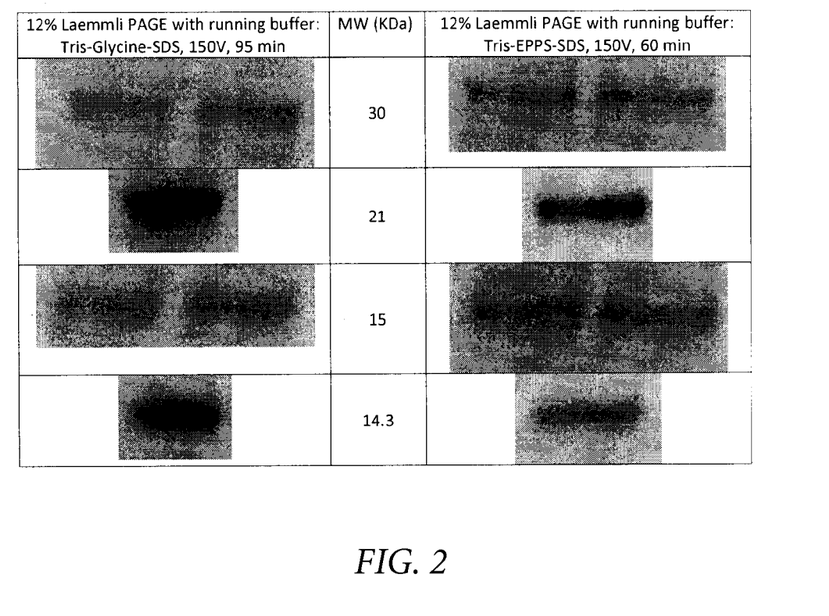
FIG. 2 illustrates polyacrylamide gels electrophoresed in electrolyte solution according an embodiment of the present invention.

Now referring to FIG. 2. The change in the band thickness and resolution of four low molecular weight proteins was measured. FIG. 2 shows that the presence of EPPS (or HEPPS) in the buffer helps improving the resolution by at least 50%. As well, the complete migration of each of these gels was accelerated by 30% using EPPS (or HEPPS).

EXAMPLE 2

The same electrolyte solutions tested as running buffer above can be used to prepare the acrylamide or agarose gel composition and provide increased resolution, but not necessarily separation speed.

TABLE 2

| Zwitterion | Gel size (migration length) | Running time | Resolution[1] |
|---|---|---|---|
| EPPS (or HEPPS) | 60 mm | 50 min | +++ |
| Glygly | 60 mm | 50 min | ++ |
| TGS* | 60 mm | 60 min | ++ |

EXAMPLE 3

Figure 3:
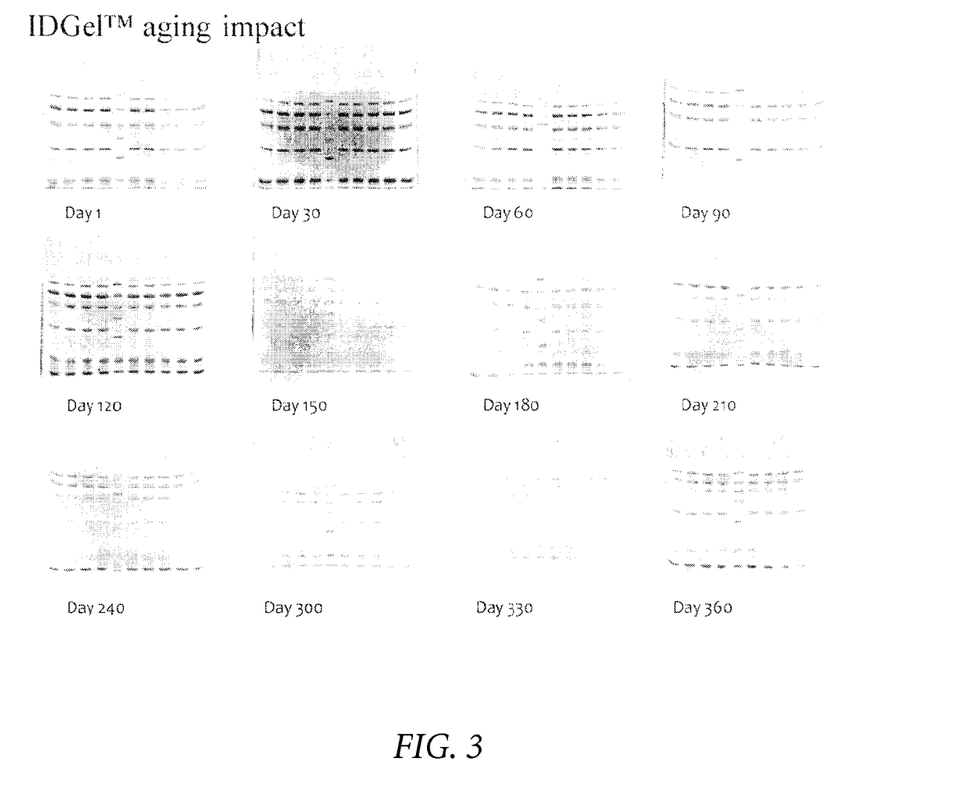
FIG. 3 illustrates polyacrylamide gels prepared with electrolyte solutions according to embodiments of the present invention, and kept at 4° C. to age during 360 days. Each month, gels were run to measure changes in resolution, migration path and migration speed.
Figure 4:
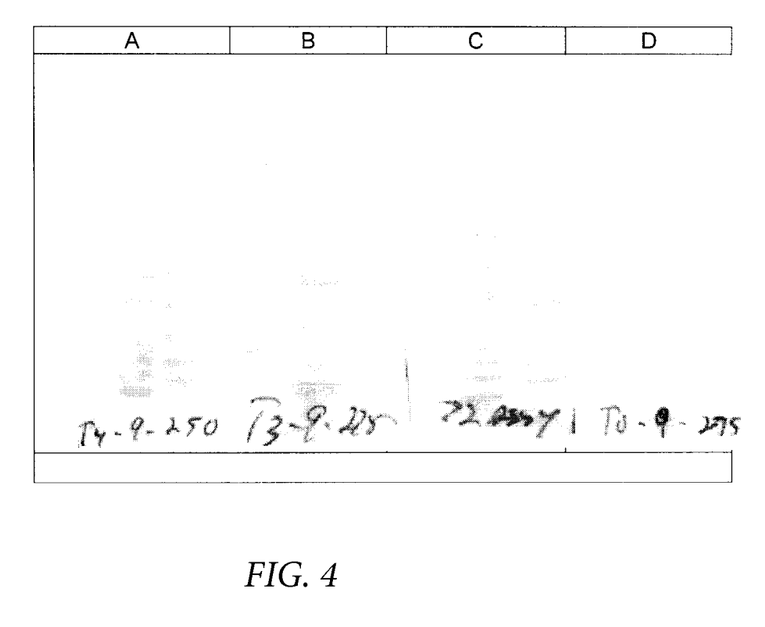
FIG. 4 illustrates membranes comprising prestained protein marker that have been transferred from polyacrylamide gels by (A) wet transfer, (B) semi-dry transfer, (C) asymmetric buffer for a "dry" transfer, and (D) a control semi-dry transfer using the classic Towbin buffer, run 275 mA for 15 minutes. The transfer in D is not as efficient. The run prestained protein markers range from 6KDa to 245 KDa.
Figure 5:
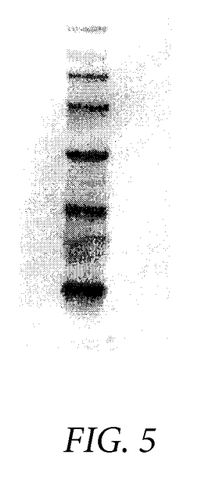
FIG. 5 illustrates a prestained protein marker that have been transferred from polyacrylamide gels in the eStain™ apparatus using a 5× solution of an EPPS (or HEPPS) containing buffer according to the present invention.

Some of these compounds have been identified to have a positive impact on stabilizing the gel matrix and allowing an extended storage, or more stable aging, providing longer shelf-life at 4° C. or room temperature. Now referring to FIG. 3. The figure shows that gels kept at 4° C. and tested every 30 days to detect the impact of aging. The results show that after 360 days, the gel migration is similar to a fresh 1-day old precast gel. These results confirm the stability of the gel matrix when EPPS (or HEPPS) is used as a buffering agent.

EXAMPLE 4

The buffer of the present invention may also be used a transfer buffer in applications such as the transfer of proteins from acrylamide gels (Western transfer). Exemplary buffers were prepared according to table 3, below.

TABLE 3

| | # | | | | |
|---|---|---|---|---|---|
| Compound | T0 | T1 | T2 | T3 | T4 |
| Tris (g) | 3 | 18 | 3 | 9 | 6 |
| Glycine (g) | 14.4 | — | — | — | — |
| EPPS (or HEPPS) (g) | — | 12 | 2 | 6 | 4 |
| H$_2$O (ml) to | 800 | 800 | 800 | 800 | 800 |
| Methanol (ml) | 200 | 200 | 200 | 200 | 200 |

T0 = Laemmli buffer with a glycine base.

Transfer of protein markers from a precast IDGel™ (made with Tris pH 8.3 as buffering solution). The transfer was most efficient with the recipe of buffer T4.

EXAMPLE 5

Several buffers according to the present invention are tested. The zwitterions tested are listed in table 4

TABLE 4

| | Testing of zwitterions of interest | | |
|---|---|---|---|
| Composants | Symetrical | Cathode | Anode |
| Tris (g) | 6 | 6 | 1 |
| EPPS (or HEPPS) (g) | 4 | 1 | 4 |
| Gly-Gly (g) | 4 | 1 | 4 |
| CAPSO (g) | 4 | 1 | 4 |
| BES (g) | 4 | 1 | 4 |
| Methanol | 0% 10% 20% | 0% 10% 20% | 0% 10% 20% |
| Total volume | 1 litre | 1 litre | 1 litre |

The transfer efficacy of the different tested zwitterions are:

| EPPS (HEPPS) | 100% |
|---|---|
| Gly-Gly | 100% |
| CAPSO | 90% |
| BES | 80% |

EXAMPLE 6

Several buffers according to the present invention are tested in an asymmetric configuration, as indicated in table 5.

TABLE 5

| transfer of asymmetric buffer: | | |
|---|---|---|
| Components | Cathode | Anode |
| Tris (g) | 6 | 1 |
| Gly-Gly (g) or EPPS (or HEPPS) | 1 | 6 |
| Methanol | 10% | 10% |

In each case, for the presented asymmetric arrangements with Gly-gly or EPPS (or HEPPS) buffer, the transfer is 100% efficient and occurs in 15 min of electrophoresis.

EXAMPLE 7

The Tris/Gly-Gly buffer according to the present invention (see Example 5) may be used for Western transfer without any further modification. The buffer also supports an accelerated separation/transfer: a current of 275 mA results in a complete transfer in 15 minutes or less. Methanol is normally added to the transfer buffer to slow the protein migration and normally permit a more equal protein transfer between the high molecular weight proteins and the low molecular weight. In standard protocol, it is used as 10% or 20% of methanol. The efficacy of fast transfer with electrolyte solutions according to the present invention containing 0% to 20% methanol is working equally well to 100% efficacy in transfer under all these conditions.

EXAMPLE 8

To perform semi-dry and/or wet transfer, the an electrolyte solution according to the present invention may be used. The solution containing EPPS (or HEPPS) is prepared as a 0.3× solution: 6 g Tris, 4 g EPPS (or HEPPS) in a total volume of 1 L of distilled water. The electrolyte solution may comprise between 0% to 20% methanol, and preferably between 10 and 20% methanol to improve transfer of large molecular weight proteins. The transfer of sample from the gel at 275 mA is typically completed in 10 to 15 minutes.

EXAMPLE 9

For use in electrophoresis transfer system such as the eStain™ since the volume of electrolyte solution required is small, two blotting papers are soaked in a 5× electrolyte solution according to the present invention (90 g Tris, 60 g EPPS (or HEPPS) and up to a 1 L total volume with water) and are placed on each side of the gel from which the proteins are transferred. The transfer is complete in 10 minutes at about 80 mA to about 300 mA, 100% of the sample is transferred to the PVDF membrane used.

EXAMPLE 10

Improved Buffer for Mops Based Gels

A protein electrophoresis running buffer that accelerates the separation speed and increase resolution of MOPS based gels and other gels. The buffer is based on the Tris-EPPS-SDS buffer in combination with the ACES, MOPS, and PIPES zwitterions This buffer will be advantageous on gels based on a different chemistry than Laemmli's, for example MOPS based gels such as NuPage™ from Invitrogen and EZ-Run™ from ThermoFisher, chemistry proprietary to Amresco.

The basic recipe of the buffer is a combination of Tris+SDS+EPPS+ACES+MOPS+PIPES, at a pH 8.5 or less and may facultatively include one anionic surfactant to provide to the buffer denaturing properties for protein analysis (e.g. SDS, sodium dodecyl sulphate, Sodium lauryl sulfate (SLS), sodium laurilsulfate or sodium, NaDS).

The proportions of this electrolyte solution are as indicated in table 6:

TABLE 6

Components of the composition

|  | % weight | mM 1X |
|---|---|---|
| TRIS | 49.9% | 74.3 |
| SDS | 2.8% | 3.5 |
| EPPS | 19.4% | 27.7 |
| ACES | 9.7% | 19.2 |
| PIPES | 1.7% | 2.0 |
| MOPS | 16.6% | 95.6 |

Under such proportion, the buffer has a pH of 7.4, which is compatible with the MOPS based gels having a pH of 7.0.

EXAMPLE 11

Improved Buffer for Mops Based Gels

This study was made using the liquid gel matrix EZ-Run™ from ThermoFisher™, a product developed by Amrescon™ This liquid gel matrix has the advantage to be stable over one year at room temperature and allow to quickly cast electrophoresis gels. The gel matrix comes with its specific running buffer, which has to be used with it. The recommended running conditions are 150V.

The main problem related to this liquid gel matrix is that it takes longer than a normal Laemmli gel or other precast gels available on the market to make a normal gel separation. For this reason, the EPPS based running buffer of the present invention is adapted to this MOPS based gel matrix (see US Patent publication No. 20060118418).

The performances of the new buffer are represented in the following table. "Long gel"=10×10 cm and "Short gel"=10×8.2 cm.

TABLE 7

| Performance EZ-Run vs IDFast Univ | | |
|---|---|---|
| Long gel 150 V | | |
| EZRun | 110 min | |
| EPPS mix | 80 min | 27% faster |
| Long gel 200 V | | |
| EZRun | 80 min | |
| EPPS mix | 50 min | 38% faster |

TABLE 7-continued

| Performance EZ-Run vs IDFast Univ | | |
|---|---|---|
| Short gel 150 V | | |
| EZRun | 65 min | |
| EPPS mix | 45 min | 31% faster |
| Short gel 200 V | | |
| EZRun | 50 min | |
| EPPS mix pH 7.4 | 35 min | 30% faster |
| EPPS mix 2 pH 8 | 30 min | 40% faster |
| Also compatible with Laemmli gels (short gels, 200 V) | | |
| EZRun | 50 min | |
| EPPS only buffer | 35 min | |
| EPPS mix | 29 min | 17% faster |
| EPPS mix pH 7.4 | 29 min | |

Figure 6:
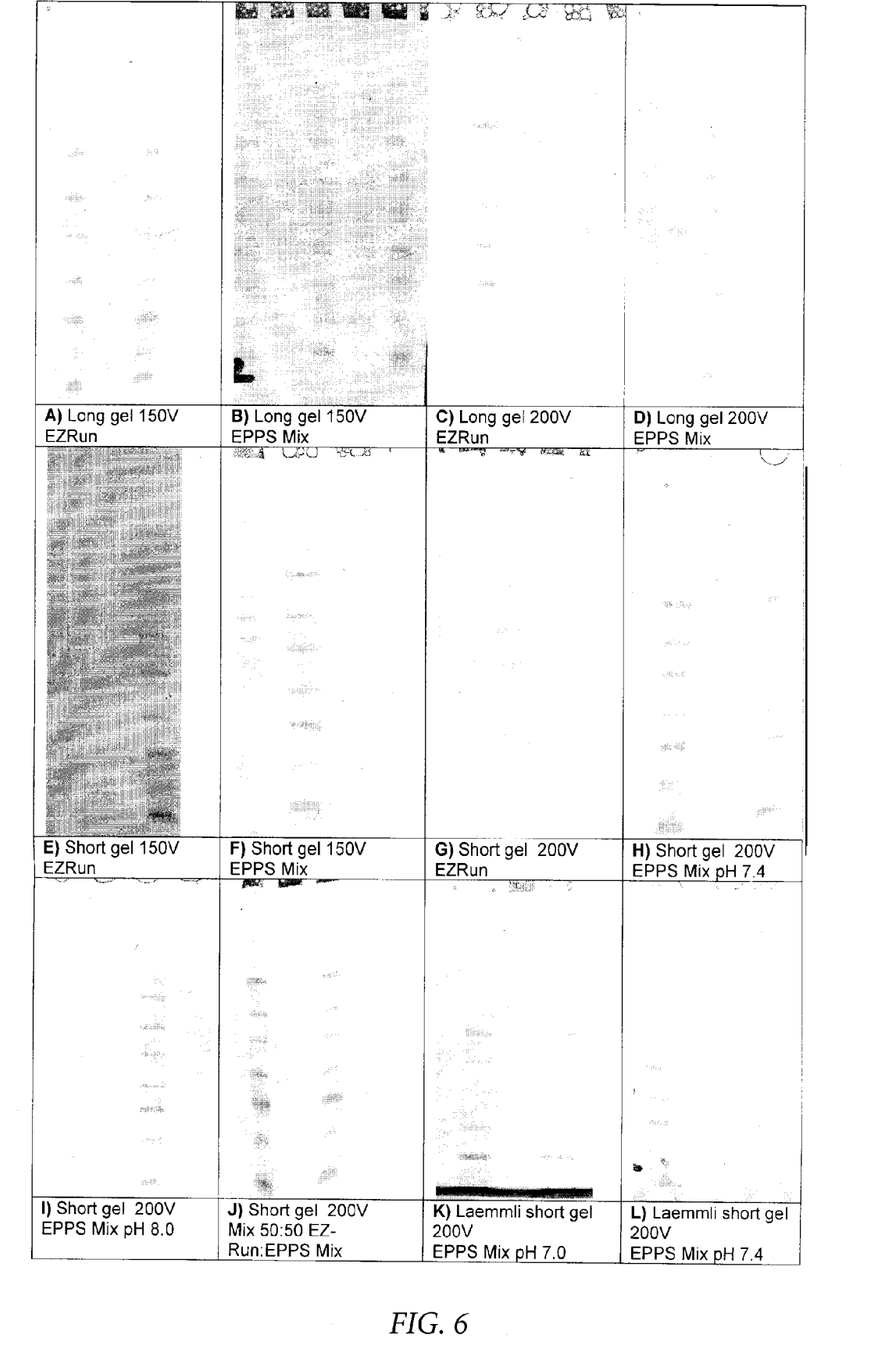
FIG. 6 (A-L) illustrates a comparison of the migration resolution of MOPS based gels in an electrolyte solutions according to the present invention vs. the regular running buffer for the MOPS based gels.

The gel prepared with the EZ-Run gel matrix and migrated with the EZ-Run specific running buffer, when compared to the EPPS based buffer of the present invention, as described in Example 9, clearly shows an advantage in migration speed for the electrolyte solution of the present invention without loss of resolution (See. FIG. 6).

The pH of the electrolyte solution will also affect the speed. The EZ-Run gel matrix has a pH of 7.0. The EZ-Run running buffer has a pH of 8.0. The electrolyte solution of the present invention (according to Example 9) has a pH of 7.4 once mixed, but adjusting it to 8.0 with NaOH has an important impact on the speed.

The electrolyte solution of the present invention can be used alone, as well as in combination with the buffer specifically designed for this gel matrix (EZ-Run running buffer in this example). The proportion can change as desired, and shows compatibility in the resolution and a proportional speed of migration. Based on the results above, it appears that the EZ-Run buffer slows down the migration.

EXAMPLE 12

Improved Resolution and Gradient Effect of EPPS Based Gels

Figure 7A:
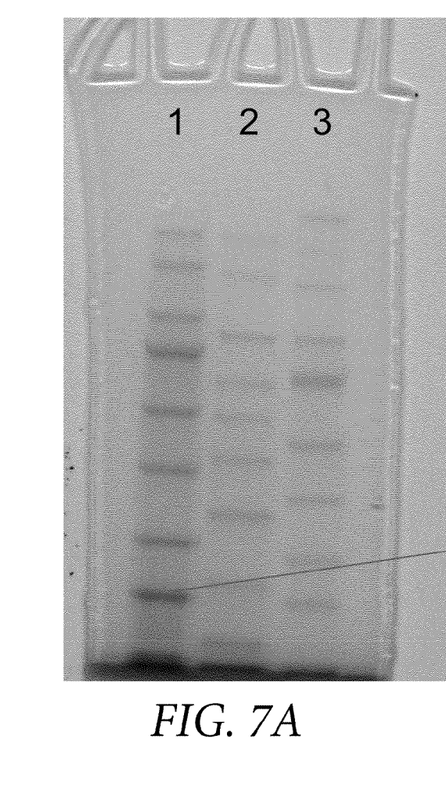
Figure 7B:
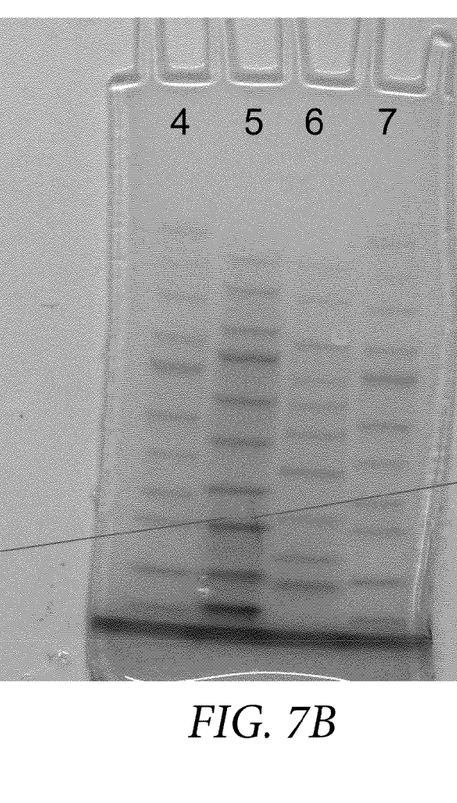
Figure 7C:
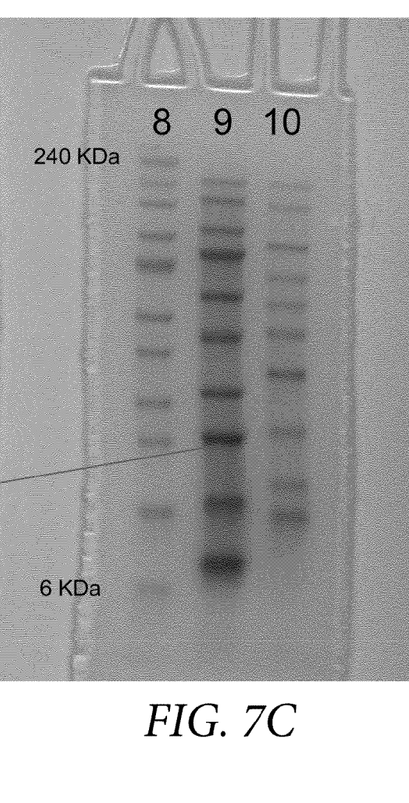

An electrolyte solution according to the present invention is identified to have a positive impact on the resolution of the protein bands separated on the gel. The electrolyte solution improves both the definition (sharpness) and the separation of the protein bands separated. Now referring to FIGS. 7A, B and C, three polyacrylamide gels were prepared. Gel A is a precast IDGel™ Tris-Glycine gel with 10% acrylamide; gel B is an IDGel™ Tris-Glycine gel with a gradient of 4% to 20% acrylamide; gel C is a gel containing 50 mM EPPS with 10% acrylamide, according to the present invention. All gels were run in a 50 mM EPPS and 50 mM Tris containing buffer (IDFast) according to the present invention. FIG. 7 shows that compared to the Tris-glycine gels, the resolution of the EPPS gel is much improved. The band linked by a line corresponds to 25 kDa.

For example the EPPS containing gel (FIG. 7C) is capable of resolving proteins better than a Tris-glycine gel of identical acrylamide percentage (compare FIGS. 7A and C, lanes 1 vs. 9, lanes 2 vs. 10, and lanes 3 vs. 8). It may be observed that the smaller molecular weight proteins (e.g. 6 kDa in lanes 3 and 8, 10 kDa and 17 kDa in lanes 1 and 9 and 19 kDa and 15 kDa in lanes 2 and 10) are well distanced and distinguishable on EPPS containing gel, while they are poorly separated and fused with the dye front in the Tris-glycine gel. Furthermore, higher molecular weight bands are somewhat sharper.

Also, the EPPS containing gel (FIG. 7C) is also capable of providing better resolution than a Tris-glycine gradient (4 to 20% acrylamide) gel (FIG. 7B). The gradient gel of FIG. 7B provides distinctly better resolution than that of the Tris-glycine 10% gel, providing separation of the smaller molecular weight proteins (compare lanes 1 and 5, 2 and 6, and 3 to 4 and 7). Nevertheless, when compared to the gradient gel, the EPPS containing gel (compare FIGS. 7B and C) provides for greater distance between the protein bands across the entire range of molecular weight, especially for the smaller molecular weight proteins. The EPPS containing gel permits for small differences in molecular weight of protein to be made (e.g. compare lanes 4-5 to lanes 8-9. Interestingly, the EPPS containing gel appears to migrate in a similar "gradient-like" manner that is more commonly observed in gradient gels such as in FIG. 7B, this without the presence of a gradient in the EPPS containing gel, which is of a fixed 10% acrylamide concentration. Note that the dye migration front of the EPPS containing gel (FIG. 7C) has already exited the gel, while it remains present in the other gels.

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed.

The invention claimed is:

1. An electrolyte solution comprising:
   Tris(hydroxymethyl)aminomethane (TRIS);
   at least one zwitterion chosen from 2-amino-2methyl-1,3-propanediol (AMPD), N,N-bis[2-hydroxyethyl]-2-aminoethanesulphonic acid (BES), N-Glycylglycine (Gly-Gly), 4-(2-hydroxyethyl)piperazine-1-propanesulfonic acid (EPPS or HEPPS), and 3-(cyclohexylamino)-2-hydroxy-1-propanesulfonic acid (CAPSO), N-(1,1-Dimethyl-2-hydroxyethyl)-3-amino-2-hydroxypropanesulfonic acid (AMPSO), 3-(cyclohexylamino)-1-propanesulfonic acid (CAPS), 2-(cyclohexylamino)ethanesulfonic acid (CHES), 3-[N-Bis(hydroxyethyl)amino]-2-hydroxypropanesulfonic acid (DIPSO), N-(2-Hydroxyethyl)piperazine-N'-(4-butanesulfonic acid) (HEPBS), 4-(N-Morpholino)butanesulfonic acid (MOBS), piperazie-N,N'-bis[2-hydroxypropanesulphonic]acid (POPSO), N-Tris(hydroxymethyl)methyl-4-aminobutanesulfonic acid (TABS), N-Tris(hydroxymethyl)methyl-3-aminopropanesulfonic acid (TAPS), (2-[2-hydroxy-1,1-bis(hydroxymethyl)ethylamino]ethanesulphonic acid) (TES), (2-[2-acetamino]-2-aminoethanesulphonic acid) (ACES), (1,4-piperazinediethanesulphonic acid) (PIPES), and Piperazine-N,N'-bis(3-propanesulfonic Acid) (PIPPS);
   water, and
   at least one of
   methanol,
   0.5% (wt/vol) or less sodium dodecyl sulphate (SDS), or methanol and 0.5% (wt/vol) or less sodium dodecyl sulphate (SDS);
   wherein the pH of the electrolyte solution is from about 8.0 to about 8.8,
   wherein said electrolyte solution is for at least one of:
   a shorter electrophoresis time of a gel electrophoresis,
   an improved resolution of a gel electrophoresis,
   an improved transfer efficacy of a gel electrophoresis, and
   a shorter transfer time of a gel electrophoresis,
   compared to a Tris-Glycine-SDS electrolyte solution at pH 8.3.

2. The electrolyte solution of claim 1, wherein said methanol is up to 20%.

3. The electrolyte solution of claim 1, further comprising a chelating agent having the name: ethylenediaminetetraacetate (EDTA), ethylene glycol tetraacetic acid (EGTA), trisodium nitrilotriacetate, hydroxyethyl ethylenediamine trisodium acetate (trisodium HEDTA), diethylene triamino pentasodium acetate or uramil disodium acetate.

4. The electrolyte solution of claim 1, wherein the concentration of Tris(hydroxymethyl)aminomethane (TRIS) is from about 10 mM to about 500 mM.

5. The electrolyte solution of claim 1, wherein the concentration of the zwitterion is from about 1 mM to about 500 mM.

6. The electrolyte solution of claim 5, wherein the concentration of Tris(hydroxymethyl)aminomethane (TRIS) is from about 50 mM to about 150 mM.

7. The electrolyte solution of claim 5, wherein the concentration of Tris(hydroxymethyl)aminomethane (TRIS) is from about 50 mM to about 250 mM.

8. The electrolyte solution of claim 5, wherein the concentration of Tris(hydroxymethyl)aminomethane (TRIS) is 150 mM.

9. The electrolyte solution of claim 1, wherein the concentration of sodium dodecyl sulphate (SDS) is 0.1% (wt/vol) or less.

10. The electrolyte solution of claim 3, wherein the concentration of ethylenediaminetetraacetate (EDTA) is 0.5% (wt/vol) or less.

11. The electrolyte solution of claim 10, wherein the concentration of ethylenediaminetetraacetate (EDTA) is 0.05% (wt/vol) or less.

12. The electrolyte solution according to claim 1, wherein said zwitterions is a combination of 4-(2-hydroxyethyl)piperazine-1-propanesulfonic acid (EPPS or HEPPS), (2-[2-acetamino]-2-aminoethanesulphonic acid) (ACES), and (1,4-piperazinediethanesulphonic acid) (PIPES).

13. An electrophoresis gel comprising the electrolyte solution of claim 1, wherein the gel is chosen from an acrylamide gel, at a concentration from less than 1% (wt/vol) to about 25% (wt/vol), an agarose gel at a concentration from about 0.5% (wt/vol) to about 3% (wt/vol) and a combination gel thereof, wherein the concentration of acrylamide is from.

14. The electrophoresis gel of claim 13, further comprising sodium dodecyl sulphate (SDS).

15. The electrophoresis gel of claim 13, wherein the pH is from about 8.0 to about 8.8.

16. A method of accelerating or improving the resolution, or improving transfer efficacy, or accelerating and improving the resolution, or accelerating and improving transfer efficacy of the electrophoretic separation of at least one sample comprising the step of:
   applying a voltage to an electrolyte solution according to claim 1, in contact with an electrophoresis gel containing the at least one sample therein.

* * * * *